(12) United States Patent
Chapman et al.

(10) Patent No.: US 6,348,570 B1
(45) Date of Patent: Feb. 19, 2002

(54) CHROMOPHORE CONTAINING COMPOUNDS AND THEIR USE IN DETERMINING INTERLEUKIN-1β CONVERTASE ACTIVITY

(75) Inventors: Kevin T. Chapman, Scotch Plains; Malcolm Maccoss, Freehold; Richard A. Mumford, Red Bank; Nancy A. Thornberry, Westfield; Jeffrey R. Weidner, Iselin; William K. Hagmann, Westfield, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 07/808,994

(22) Filed: Dec. 17, 1991

Related U.S. Application Data

(63) Continuation-in-part of application No. 07/746,455, filed on Aug. 16, 1991.

(51) Int. Cl.[7] .................. A61K 38/04; A61K 38/06; A61K 38/00
(52) U.S. Cl. .................. 530/330; 530/331; 514/18; 514/19
(58) Field of Search .................. 530/330, 331; 514/18, 19

(56) References Cited

U.S. PATENT DOCUMENTS

| 4,440,678 A | * 4/1984 | Svendsen |
| 5,055,451 A | 10/1991 | Krantz et al. |

FOREIGN PATENT DOCUMENTS

| WO | WO 91/15577 | 10/1991 |
| WO | 9115577 | * 10/1991 |

OTHER PUBLICATIONS

Sleath et al. J. Biol. Chem. vol. 265 No. 24 (8/96) 14526–14528.*
Toyohara et al. Agric. Biol. Chem. vol. 50(8) 2131–2132 (1986).*
Peptide, Supplemental Price List, Spring 1993.
Black, et al J. Biol. Chem. 263, 9437–9442 (1988).
Black, et al J. Biol. Chem. 264, 5323–5326 (1989).
Black, et al FEB LETT. 247, 286–290 (1989).
Kostura, et al Proc. Natl. Acad. Sci. 86, 5227–5231 (1989).
Sleath, et al J. Biol. Chem. 265, 14526–14528 (1990).

* cited by examiner

*Primary Examiner*—Yvonne Eyler
(74) *Attorney, Agent, or Firm*—Raynard Yuro; Curtis C. Panzer; David L. Rose

(57) ABSTRACT

Disclosed are novel chromophore containing compounds of Formula I and their use in determining interleukin-1β convertase (ICE) activity. ICE has been implicated in inflammatory or immune-based diseases of the lung and airways; central nervous system and surrounding membranes; the eyes and ears; joints, bones, and connective tissues; cardiovascular system including the pericardium; the gastrointestinal and urogenital systems; the skin and mucosal membranes.

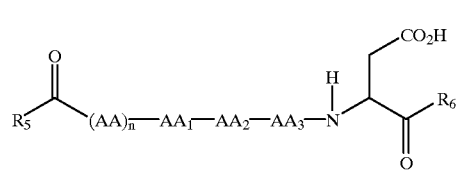

10 Claims, No Drawings

CHROMOPHORE CONTAINING COMPOUNDS AND THEIR USE IN DETERMINING INTERLEUKIN-1β CONVERTASE ACTIVITY

This is a continuation-in-part of U.S. Ser. No. 07/746,455 filed Aug. 16, 1991.

BACKGROUND OF THE INVENTION

The instant invention concerns novel chromophore containing compounds useful in determining Interleukin-1β convertase activity. Interleukin-1β convertase (ICE) has been identified as the enzyme responsible for converting precursor interleukin-1β (IL-1β) to biologically active IL-1β. Compounds of Formulas I and II are useful in the diagnosing and monitoring IL-1 mediated dieases or in evaluation inhibitors of interleukin-1β convertase.

Mammalian interleukin-1 (IL-1) is an immunoregulatory protein secreted by cell types as part of the inflammatory response. The primary cell type responsible for IL-1 production is the peripheral blood monocyte. Other cell types have also been described as releasing or containing IL-1 or IL-1 like molecules. These include epithelial cells (Luger, et al., J. Immunol. 127: 1493–1498 (1981), Le et al., J. Immunol. 138: 2520–2526 (1987) and Lovett and Larsen, J. Clin. Invest. 82: 115–122 (1988), connective tissue cells (Ollivierre et al., Biochem. Biophys. Res. Comm. 141: 904–911 (1986), Le et al, J. Immunol. 138: 2520–2526 (1987), cells of neuronal origin (Giulian et al., J. Esp. Med. 164: 594–604 (1986) and leukocytes (Pistoia et al., J. Immunol. 136: 1688–1692 (1986), Acres et al., Mol. Immuno. 24: 479–485 (1987), Acres et al., J. Immunol. 138: 2132–2136 (1987) and Lindenmann et al., J. Immunol 140: 837–839 (1988).

Biologically active IL-1 exists in two distinct forms, IL-1α with an isoelectric point of about pI 5.2 and IL-1β with an isoelectric point of about 7.0 with both forms having a molecular mass of about 17,500 (Bayne et al., J. Esp. Med. 163: 1267–1280 (1986) and Schmidt, J. Esp. Med. 160: 772 (1984). The polypeptides appear evolutionarily conserved, showing about 27–33% homology at the amino acid level (Clark et al., Nucleic Acids Res. 14: 7897–7914 (1986).

Mammalian IL-1 is synthesized as a cell associated precursor polypeptide with a molecular mass of about 31.4 kDa (Limjuco et al., Proc. Natl. Acad. Sci USA 83: 3972–3976 (1986). Precursor IL-1β is unable to bind to IL-1 receptors and is biologically inactive (Mosley et al., J. Biol. Chem. 262: 2941–2944 (1987). Biological activity appears dependent upon some form of proteolytic processing which results in the conversion of the precursor 31.5 kDa form to the mature 17.5 kDa form. Evidence is growing that by inhibiting the conversion of precursor IL-1β to mature IL-1β, one can effectively inhibit the activity of interleukin-1.

Mammalian cells capable of producing IL-1β include, but are not limited to, karatinocytes, endothelial cells, mesangial cells, thymic epithelial cells, dermal fibroblasts, chondrocytes, astrocytes, glioma cells, mononuclear phagocytes, granulocytes, T and B lymphocytes and NK cells.

As discussed by J. J. Oppenheim, et al. Immunology Today, vol. 7(2):45–56 (1986), the activities of interleukin-1 are many. It has been observed that catabolin, a factor that promotes degradation of cartilage matrix, also exhibited the thymocyte comitogenic activities Qf IL-1 and stimulates chondrocytes to release collagenase neutral proteases and plasminogen activator. In addition, a plasma factor termed proteolysis inducing factor stimulates muscle cells to produce prostaglandins which in turn leads to proteolysis, the release of amino acids and, in the long run, muscle wasting, and appears to represent a fragment of IL-1 with fever-inducing, acute phase response and thymocyte co-mitogenic activities.

IL-1 has multiple effects on cells involved in inflammation and wound healing. Subcutaneous injection of IL-1 leads to margination of neutrophils and maximal extravascular infiltration of the polymorphonuclear leukocytes (PMN). In vitro studies reveal IL-1 to be a chemotactic attractant for PMN to activate PMN to metabolize glucose more rapidly to reduce nitroblue tetrazolium and to release their lysozomal enzymes. Endothelial cells are stimulated to proliferate by IL-1 to produce thromboxane, to become more adhesive and to release procoagulant activity. IL-1 also enhances collagen type IV production by epidermal cells, induces osteoblast proliferation and alkaline phosphatase production and stimulates osteoclasts to resorb bone. Even macrophages have been reported to be chemotactically attracted to IL-1 to produce prostaglandins in response to IL-1 and to exhibit a more prolonged and active tumoricidal state.

IL-1β is also a potent bone resorptive agent capable upon infusion into mice of causing hypercaleemia and increas in bone resorptive surface as revealed by his to morphometry Sabatini, M. et al., PNAS 85: 5235–5239, 1988.

Accordingly, IL-1 has been implicated in infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis. Immune-based diseases which may be responsive to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis. IL-1 has also been implicated in the treatment of bone and cartilage resorption as well as diseases resulting in excessive deposition of extracellular matrix. Such diseases include periodonate diseases interstitial pulmonary fibrosis, cirrhosis, systemic sclerosis, and keloid formation.

SUMMARY OF THE INVENTION

Disclosed are novel chromophore containing compounds of Formula I and their use in determining interleukin-1β convertase (ICE) activity. Compounds of Formula II are useful in the diagnosing and monitoring IL-1 mediated dieases or in evaluation inhibitors of interleukin-1β convertase.

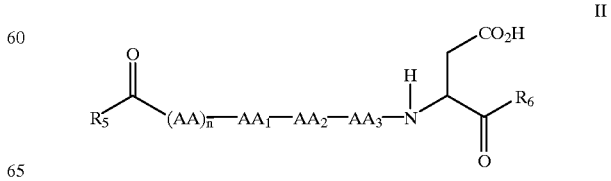

DETAILED DESCRIPTION OF THE INVENTION

In one embodiment the invention concerns a chromophore compound of Formula I

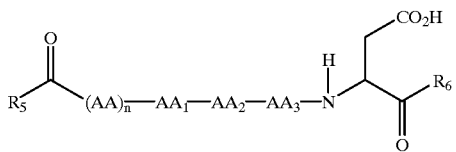

wherein:

$AA_1$, is independently selected from the group consisting of
(a) a single bond, and
(b) an amino acid of formula AI

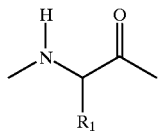

wherein $R_1$ selected from the group consisting of
(a) hydrogen,
(b) substituted $C_{1-6}$ alkyl, wherein the substituent is selected from
  (1) hydrogen,
  (2) hydroxy,
  (3) halo,
  (4) —S—$C_{1-4}$ alkyl,
  (5) —SH
  (6) $C_{1-6}$ alkylcarbonyl,
  (7) carboxy,

(8)

(9) $C_{1-4}$ alkylamino, wherein the alkyl moeity is substituted with hydrogen or hydroxy, and the amino is substituted with hydrogen or CBZ,
  (10) guanidino,
  (11) amino, and
(c) aryl $C_{1-6}$ alkyl or substituted aryl $C_{1-6}$ alkyl wherein,
  the aryl group is selected from the group consisting of:
    (a) phenyl,
    (b) naphthyl,
    (c) pyridyl,
    (d) furyl,
    (e) thienyl,
    (f) thiazolyl,
    (g) isothiazolyl,
    (h) imidazolyl,
    (i) benzimidazolyl,
    (j) pyrazinyl,
    (k) pyrimidyl,
    (l) quinolyl,
    (m) isoquinolyl,
    (n) benzofuryl,
    (o) benzothienyl,
    (p) pyrazolyl,
    (q) indolyl,
    (r) purinyl,
    (s) isoxazolyl, and
    (t) oxazolyl, and mono and di-substituted aryl as defined above in items (a) to (t) wherein the substitutents are independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;

$AA_2$ is independently selected from the group consisting of
(a) a single bond, and
(b) an amino acid of formula AII

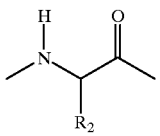

$AA_3$, which are each independently selected from the group consisting of
(a) a single bond, and
(b) an amino acid of formula AIII

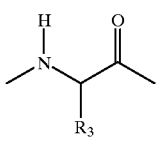

wherein $R_2$ and $R_3$ are each independently selected from the group consisting of
(a) hydrogen,
(b) substituted $C_{1-6}$alkyl, wherein the substituent is selected from
  (1) hydrogen,
  (2) hydroxy,
  (3) halo,
  (4) —S—$C_{1-4}$alkyl,
  (5) —SH
  (6) $C_{1-6}$ alkylcarbonyl,
  (7) carboxy,

(8)

(9) $C_{1-4}$ alkylamino, wherein the alkyl moeity is substituted with hydrogen or hydroxy, and the amino is substituted with hydrogen or CBZ,
  (10) guanidino,
  (11) amino, and
(c) aryl $C_{1-6}$ alkyl,
wherein aryl is defined as immediately above, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;

n is an interger from 0–16 and
$(AA)_n$ is a peptide of 0–16 (ie n) amino acids in length, each amino acid being independent of formula

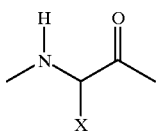

wherein X selected from the group consisting of
(a) hydrogen,
(b) substituted $C_{1-6}$ alkyl, wherein the substituent is selected from
  (1) hydrogen,
  (2) hydroxy,
  (3) halo,
  (4) —S—$C_{1-4}$ alkyl,
  (5) —SH
  (6) $C_{1-6}$ alkylcarbonyl,
  (7) carboxy, (8) 

(9) amino carbonyl amino,
  (10) $C_{1-4}$ alkylamino, wherein the alkyl moiety is substituted with hydrogen or hydroxy, and the amino is substituted with hydrogen or CBZ,
  (11) guanidino,
  (12) amino, and
(c) aryl $C_{1-6}$alkyl,
wherein the aryl group is selected from the group consisting of:
  (1) phenyl,
  (2) naphthyl,
  (3) pyridyl,
  (4) furyl,
  (5) thienyl,
  (6) thiazolyl,
  (7) isothiazolyl,
  (8) imidazolyl,
  (9) benzimidazolyl,
  (10) pyrazinyl,
  (11) pyrimidyl,
  (12) quinolyl,
  (13) isoquinolyl,
  (14) benzofuryl,
  (15) benzothienyl,
  (16) pyrazolyl,
  (17) indolyl,
  (18) purinyl,
  (19) isoxazolyl, and
  (20) oxazolyl,
and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;

$R_5$ is
(a) substituted $C_{1-12}$ alkyl, wherein the substituent is selected from
  (1) hydrogen,
  (2) hydroxy,
  (3) halo, and
  (4) $C_{1-6}$ alkylcarbonyl;
(b) aryl $C_{1-6}$ alkyl wherein the aryl group is selected from the group consisting of:
  (1) phenyl,
  (2) naphthyl,
  (3) pyridyl,
  (4) furyl,
  (5) thienyl,
  (6) thiazolyl,
  (7) isothiazolyl,
  (8) imidazolyl,
  (9) benzimidazolyl,
  (10) pyrazinyl,
  (11) pyrimidyl,
  (12) quinolyl,
  (13) isoquinolyl,
  (14) benzofuryl,
  (15) benzothienyl,
  (16) pyrazolyl,
  (17) indolyl,
  (18) purinyl,
  (19) isoxazolyl, and
  (20) oxazolyl,
and mono and di-substituted aryl as defined above in items (1) to (20) wherein the substitutents are independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.

$R_6$ is selected from the group consisting of:
  (a) mono, di or tri substituted Aryl amino,
  (b) mono, di or tri substituted Aryl oxy, and
  (c) mono, di or tri substituted Aryl thio,
wherein the aryl group is selected from the group consisting of:

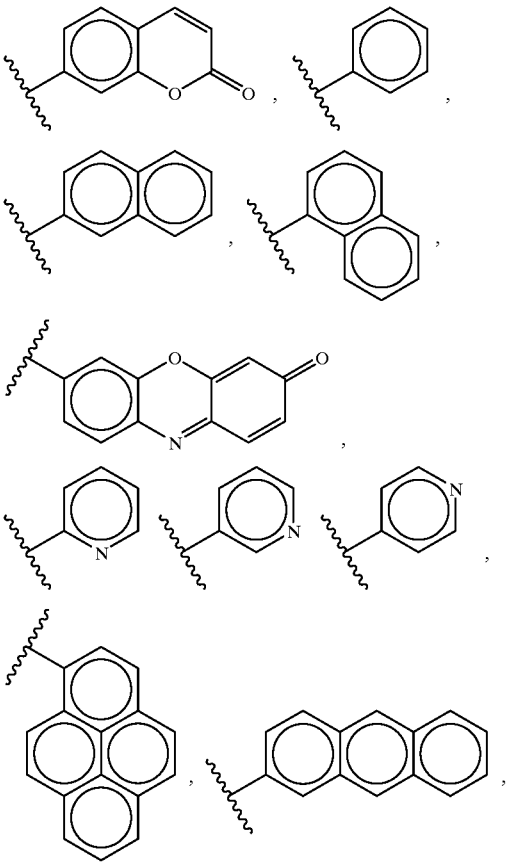

-continued

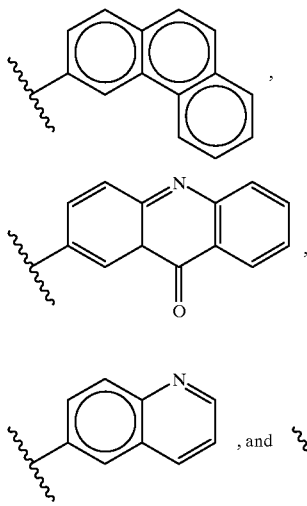

wherein the substituent is selected from the group consisting of
(1) H,
(2) OH,
(3) halo,
(4) $C_{1-6}$alkyl,
(5) $C_{1-6}$alkyloxy,
(6) $CO_2H$,
(7) $NO_2$,
(8) $SO_3H$,
(9) formyl,
(10) $NH_2$,
(11) SH,
(12) $C_{1-6}$alkylthio,

 (13)

(14) phenyl,
(15) phenyl$C_{1-6}$alkyl
(16) NO,
(17) $C_{1-6}$alkylcarbonyl,
(18) phenylazo,
(19) $C_{1-6}$sulfinyl,
(20) $C_{1-6}$sulphonyl,
(21) phenyl sulfinyl,
(22) phenyl sulfonyl,
(23) phenyl carbonyl,
(24) phenyl oxy,
(25) phenyl thiol,
(26) $C_{1-4}$alkylamino,
(27) di$C_{1-4}$alkylamino, and
(28) CN,
and $R_8$ is
$C_{1-6}$alkyl or aryl $C_{1-6}$alkyl wherein aryl is selected from the phenyl and naphthyl.

As above, $(AA)_n$ defines a peptide of 0,1,2,3,4,5,6,7,8,9, 10,11,12,13,14,15, or 16 amino acids in length. Similarly, for purposes of this specification, the amino acids AAI, AAII, and AAIII may be each independently selected from the group consisting of the L- and D- forms of the amino acids including glycine, alanine, valine, leucine, isoleucine, serine, threonine, aspartic acid, asparagine, glutamic acid, glutamine, lysine, hydroxy-lysine, histidine, arginine, phenylalanine, tyrosine, tryptophan, cysteine, methionine, ornithine, β-alanine, homoserine, homotyrosine, homophenylalanine and citrulline. Compounds of Formula I correspond to the peptide sequence which is SEQ. ID NO: 1:

In one class of the first embodiment n is 0. Within this class is the subclass
wherein
$AA_1$, is an amino acid of formula

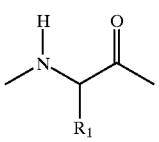

$AA_2$ is an amino acid of formula

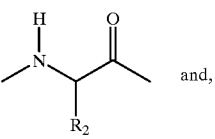 and, $AA_3$ is an amino acid of formula

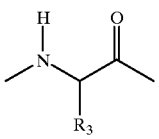

Within the subclass are the compounds wherein $R_2$ and $R_3$ are each independently selected from the group consisting of
(a) hydrogen,
(b) $C_{1-6}$alkyl, wherein the substituent is selected from
(1) hydrogen,
(2) hydroxy,
(3) halo,
(4) —S—$C_{1-4}$alkyl,
(5) —SH,
(6) $C_{1-6}$ alkylcarbonyl,
(7) carboxy,

 (8)

(9) $C_{1-4}$alkylamino, and $C_{1-4}$ alkyl amino wherein the alkyl moeity is substituted with an hydroxy, and
(10) guanidino,
(11) amino, and
(c) aryl $C_{1-6}$ alkyl,
wherein aryl is phenyl, naphthyl, pyridyl, furyl, thienyl, thiazolyl, isothiazolyl, benzofuryl, benzothienyl, indolyl, isoxazolyl, and oxazolyl; and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.

$R_6$ is selected from the group consisting of:
  (a) mono or di substituted Aryl amino,
  (b) mono or di substituted Aryl oxy, and
  (c) mono or di substituted Aryl thio,
wherein the aryl group is selected from the group consisting of:

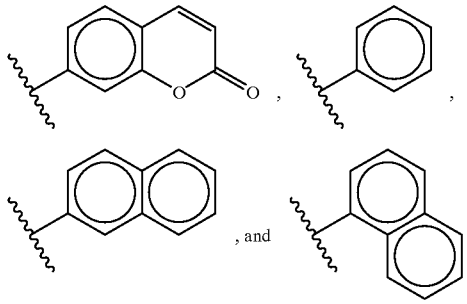

, and wherein the substituent is selected from the group consisting of
  (1) H,
  (2) OH,
  (3) halo,
  (4) $C_{1-6}$alkyl,
  (5) $C_{1-6}$alkyloxy,
  (6) $CO_2H$,
  (7) $NO_2$,
  (8) $SO_3H$,
  (9) formyl, and
  (10) CN.

More particularly, illustrating the invention are the compounds wherein: $R_5$ is methyl;
  $R_2$ is $C_{1-6}$alkyl; and
  R3 is
    (a) hydrogen,
    (b) $C_{1-6}$alkyl,
    (d) benzyl,
    (e) p-hydroxy-benzyl,
    (f) N-carbobenzoxy-amino-(n-butyl),
    (g) carbamylmethyl,
    (h) carbamylethyl,
    (i) indol-2-yl-methyl,
    (j) substituted phenyl $C_{1-6}$alkyl, wherein the substituent is hydrogen, hydroxy, carboxy, or $C_{1-4}$alkyl,
    (k) substituted indolyl $C_{1-6}$alkyl, wherein the substituent is hydrogen, hydroxy, carboxy, or $C_{1-4}$alkyl, or
    (1) substituted imidazolyl $C_{1-6}$alkyl wherein the substituent is hydrogen, hydroxy, carboxy, or $C_{1-4}$alkyl.

In a second embodiment the invention concerns a chromophore containing compound of Formula II

II

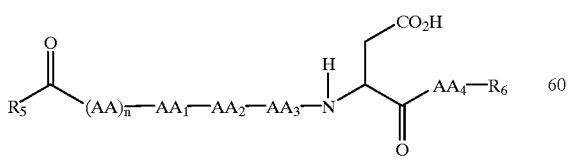

wherein:
  $AA_1$, is independently selected from the group consisting of
    (a) a single bond, and
    (b) an amino acid of formula AI

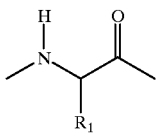

wherein $R_1$ selected from the group consisting of
  (1) substituted $C_{1-6}$ alkyl, wherein the substituent is selected from
    (a) hydrogen,
    (b) hydroxy,
    (c) halo,
    (d) $C_{1-6}$alkyl carbonyl, and
    (e) amino,
  (2) aryl $C_{1-6}$ alkyl or substituted aryl $C_{1-6}$alkyl wherein, the aryl group is selected from the group consisting of:
    (a) phenyl,
    (b) naphthyl,
    (c) pyridyl,
    (d) furyl,
    (e) thienyl,
    (f) thiazolyl,
    (g) isothiazolyl,
    (h) imidazolyl,
    (i) benzimidazolyl,
    (j) pyrazinyl,
    (k) pyrimidyl,
    (l) quinolyl,
    (m) isoquinolyl,
    (n) benzofuryl,
    (o) benzothienyl,
    (p) pyrazolyl,
    (q) indolyl,
    (r) purinyl,
    (s) isoxazolyl, and
    (t) oxazolyl, and mono and di-substituted aryl as defined above in items (a) to (t) wherein the substitutents are independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;

$AA_2$ is independently selected from the group consisting of
  (a) a single bond, and
  (b) an amino acid of formula AII

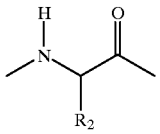

$AA_3$, which are each independently selected from the group consisting of (a) a single bond, and
(b) an amino acid of formula AIII

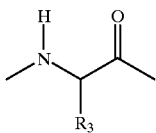

wherein $R_2$ and $R_3$ are each independently selected from the group consisting of
(a) hydrogen,
(b) substituted $C_{1-6}$alkyl, wherein the substituent is selected from
   (1) hydrogen,
   (2) hydroxy,
   (3) halo,
   (4) —S—$C_{1-4}$alkyl,
   (5) —SH
   (6) $C_{1-6}$ alkylcarbonyl,
   (7) carboxy,
   (8)

(9) $C_{1-4}$ alkylamino, wherein the alkyl moiety is substituted with hydrogen or hydroxy, and the amino is substituted with hydrogen or CBZ,
   (10) guanidino,
   (11) amino, and
(c) aryl $C_{1-6}$ alkyl,
wherein aryl is defined as immediately above, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;
  $AA_4$ is
   an amino acid of formula AIV

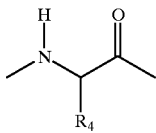

wherein $R_4$ selected from the group consisting of
(a) hydrogen, or
(b) substituted $C_{1-6}$ alkyl, wherein the substituent is selected from
   (1) hydrogen,
   (2) hydroxy,
   (3) halo,
   (4) —S—$C_{1-4}$alkyl,
   (5) —O—$C_{1-4}$alkyl
   (6) —SH
   (7) carboxy,
   (8)

(9) imidazolyl,
   (10) guanidino, and
   (11) amino;
n is an interger from 0–16 and
$(AA)_n$ is a peptide of 0–16 (ie n) amino acids in length, each amino acid being independent of formula

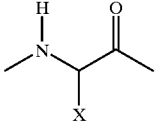

wherein X selected from the group consisting of
(a) hydrogen,
(b) substituted $C_{1-6}$ alkyl, wherein the substituent is selected from
   (1) hydrogen,
   (2) hydroxy,
   (3) halo,
   (4) —S—$C_{1-4}$alkyl,
   (5) —SH
   (6) $C_{1-6}$ alkylcarbonyl,
   (7) carboxy, 0
   (8) —CNH2,
   (9) amino carbonyl amino,
   (10) $C_{1-4}$ alkylamino, wherein the alkyl moiety is substituted with hydrogen or hydroxy, and the amino is substituted with hydrogen or CBZ,
   (11) guanidino,
   (12) amino, and
  (c) aryl $C_{1-6}$ alkyl,
wherein the aryl group is selected from the group consisting of:
   (1) phenyl,
   (2) naphthyl,
   (3) pyridyl,
   (4) furyl,
   (5) thienyl,
   (6) thiazolyl,
   (7) isothiazolyl,
   (8) imidazolyl,
   (9) benzimidazolyl,
   (10) pyrazinyl,
   (11) pyrimidyl,
   (12) quinolyl,
   (13) isoquinolyl,
   (14) benzofuryl,
   (15) benzothienyl,
   (16) pyrazolyl,
   (17) indolyl,
   (18) purinyl,
   (19) isoxazolyl, and
   (20) oxazolyl,
and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;
  $R_5$ is
   (a) substituted $C_{1-12}$ alkyl, wherein the substituent is selected from
     (1) hydrogen,
     (2) hydroxy,
     (3) halo, and
     (4) $C_{1-6}$alkylcarbonyl;
   (b) aryl $C_{1-6}$alkyl wherein the aryl group is selected from the group consisting of:
     (1) phenyl, (2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl, and
(20) oxazolyl, and mono and di-substituted aryl as defined above in items (1) to (20) wherein the substitutents are independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.

$R_6$ is selected from the group consisting of:

(a) mono di or trisubstituted Aryl amino,
(b) mono di or trisubstituted Aryl oxy, and
(c) mono di or trisubstituted Aryl oxy, wherein the aryl group is selected from the group consisting of:

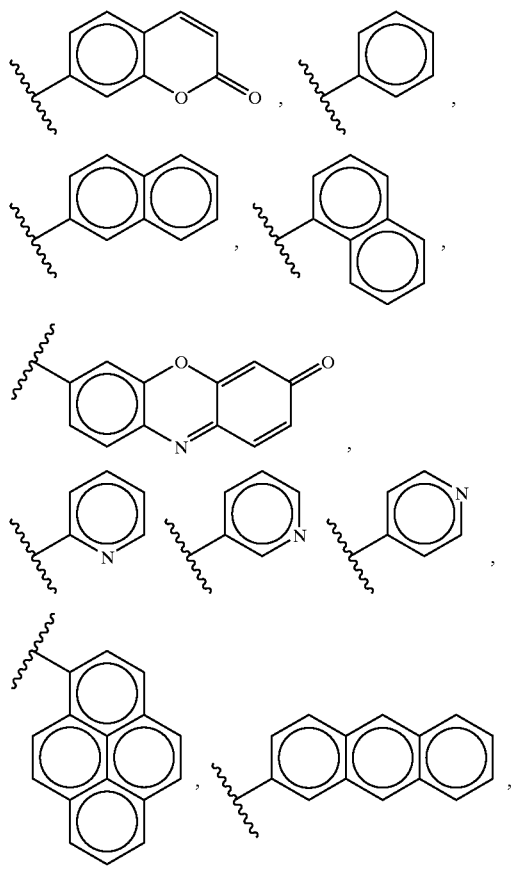

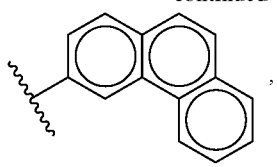

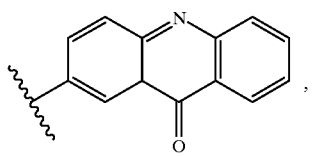

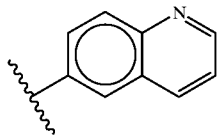 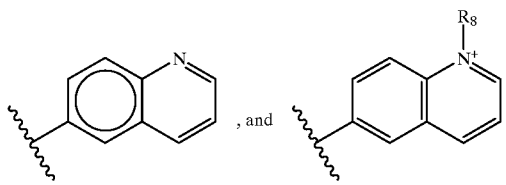

wherein the substituent is selected from the group consisting of (1) H,
(2) OH,
(3) halo,
(4) $C_{1-6}$alkyl,
(5) $C_{1-6}$alkyloxy,
(6) $CO_2H$,
(7) $NO_2$
(8) $SO_3H$
(9) formyl,
(10) $NH2$,
(11) SH,
(12) $C_{1-6}$alkylthio,

 (13)

(14) phenyl,
(15) phenyl$C_{1-6}$alkyl
(16) NO,
(17) $C_{1-6}$alkylcarbonyl,
(18) phenylazo,
(19) $C_{1-6}$sulfinyl,
(20) $C_{1-6}$sulphonyl,
(21) phenyl sulfinyl,
(22) phenyl sulfonyl,
(23) phenyl carbonyl,
(24) phenyl oxy,
(25) phenyl thiol,
(26) $C_{1-4}$alkylamino,
(27) di$C_{1-4}$alkylamino, and
(28) CN, and $R_8$ is
$C_{1-6}$alkyl or aryl $C_{1-6}$alkyl wherein the aryl is selected form the group consisting of phenyl or naphthyl.

For purposes of this specification, $(AA)_n$ defines a peptide of 0,1,2,3,4,5,6,7,8,9,10,11,12,13, 14,15, or 16 amino acids in length. Similarly, for purposes of this specification, the amino acids AAI, AAII, AAIII, and AAIV may be each independently selected from the group consisting of the L- and D- forms of the amino acids including glycine, alanine, valine, leucine, isoleucine, serine, threonine, aspartic acid, asparagine, glutamic acid, glutamine, lysine, hydroxy-lysine, histidine, arginine, phenylalanine, tyrosine, tryptophan, cysteine, methionine, ornithine, β-alanine, homoserine, homotyrosine, homophenylalanine and citrulline.

In one class of the second embodiment n is 0. Within this class is the subclass
wherein $AA_1$, is an amino acid of formula

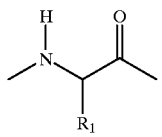

$AA_2$ is an amino acid of formula

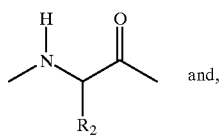

and, $AA_3$ is an amino acid of formula

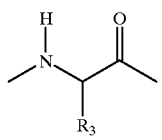

Within the subclass are the compounds wherein $R_2$ and $R_3$ are each independently selected from the group consisting of
(a) hydrogen,
(b) $C_{1-6}$alkyl, wherein the substituent is selected from
   (1) hydrogen,
   (2) hydroxy,
   (3) halo,
   (4) —S—$C_{1-4}$alkyl
   (5) —SH
   (6) $C_{1-6}$ alkylcarbonyl,
   (7) carboxy, (8)

(9) $C_{1-4}$alkylamino, and $C_{1-4}$ alkyl amino wherein the alkyl moeity is substituted with an hydroxy, and
   (10) guanidino,
   (11) amino, and
(c) aryl $C_{1-6}$alkyl, wherein aryl is phenyl, naphthyl, pyridyl, furyl, thienyl, thiazolyl, isothiazolyl, benzofuryl, benzothienyl, indolyl, isoxazolyl, and oxazolyl; and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.

$R_6$ is selected from the group consisting of:
(a) mono or di substituted Aryl amino,
(b) mono or di substituted Aryl oxy, and
(c) mono or di substituted Aryl oxy,
wherein the aryl group is selected from the group consisting of:

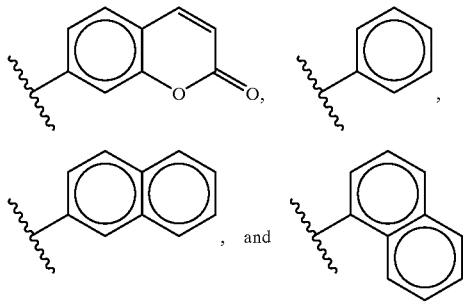

, and wherein the substituent is selected from the group consisting of
(1) H,
(2) OH,
(3) halo,
(4) $C_{1-6}$alkyl,
(5) $C_{1-6}$alkyloxy,
(6) $CO_2H$,
(7) $NO_2$,
(8) $SO_3H$,
(9) formyl, and
(10) CN.

More particularly, illustrating the invention are the compounds wherein:
$R_5$ is methyl;
$R_2$ is $C_{1-6}$alkyl; and
R3 is
(a) hydrogen,
(b) $C_{1-6}$alkyl,
(d) benzyl,
(e) p-hydroxy-benzyl,
(f) N-carbobenzoxy-amino-(n-butyl),
(g) carbamylmethyl,
(h) carbamylethyl,
(i) indol-2-yl-methyl,
(j) substituted phenyl $C_{1-6}$alkyl, wherein the substituent is hydrogen, hydroxy, carboxy, or $C_{1-4}$alkyl,
(k) substituted indolyl $C_{1-6}$alkyl, wherein the substituent is hydrogen, hydroxy, carboxy, or $C_{1-4}$alkyl, or
(l) substituted imidazolyl $C_{1-6}$alkyl wherein the substituent is hydrogen, hydroxy, carboxy, or $C_{1-4}$alkyl.

In a third embodiment, the invention concerns a method of using a chromophore containing compound of formula I for determining the interleukin-1β converting enzyme activity of a sample, comprising:
(a) adding, in aqueous solution, in any order, (1) a compound of formula I, (2) interleukin-1β converting enzyme, and
(3) said sample; and
(b) measuring the interleukin-1β converting enzyme activity of the product of step (a) by photometric means.

The useful concentration of compound of Formula I in aqueous solution is 1 μM to 10 mM. Typically, stock solutions are prepared in an organic solvent, such as DMSO, ethanol or isopropanol and diluted at least 20-fold in aqueous solution to achieve the desired concentration of substrate in the reaction mixture. The enzyme tolerates concentrations of some organic solvents (ethanol, isopropanol, DMSO) up to 20% (vol/vol) with no significant loss of enzyme activity. The choice of solvent is dictated entirely by the concentration desired in the assay, and the solubility of the substrate. Alternatively, the substrate stock solution could be prepared in buffer at a dilute concentration, and comprise a large percentage of the final reaction mixture.

Similarly, it is preferred that the aqueous solution comprises a buffer.

The pH optimum for ICE is between 6.5 and 7.5. Consequently, suitable buffer will have a pKa between 6.5 and 7.5, such as HEPES, which we use in our studies. In general, any nonreactive buffer at a concentration that will maintain the pH of the reaction between 6 and 9 will work.

Other components may be added to the reaction that stabilize the enzyme or increase the rate of the reaction. Examples are sucrose (10%), CHAPS (0.1%), DTT (1–100 mM), BSA (0.1–10 mg/ml) all of which have been demonstrated to stabilize the enzyme. Others components which may be included are glycerol, EDTA, and a variety of standard protease inhibitors.

The concentration of ICE is highly variable and may range from 1pM to 1 $\mu$M, depending entirely on the purpose of a particular experiment, and the kinetic parameters for the chosen substrate. The volume added to a particular reaction may be very small or comprise the entire volume of the reaction less the volume of substrate required to achieve the desired concentration.

Enzyme for use in the method may be obtained from any cell capable of secreting IL1B such as those listed in the Background of the Invention. Any state of purity of ICE is acceptable (including crude cell lysates), as long as the preparation is free of contaminating proteases that will compete with ICE for cleavage of the substrate. Even in this case it is possible to use this assay if inhibitors of the contaminating proteases are included in the reaction.

The sample will typically comprise either, a putative ICE inhibitor, in a concentration of 1pM to 1M or any other modulator of ICE activity.

This assay is typically run between 25 and 37 degrees. The use of higher temperatures will depend upon the stability of the enzyme and running the assay at low temperatures will probably be dictated by practical considerations.

As appreciated by those of skill in the art, addition step (a) results in the cleavage of compound of formula I between the aspartic acid specifically described, and the adjacent group, $R_6$. The liberation of the chromophoric group, $R_6$ may be monitored by spectrophotometric or fluorometric procedures.

The method of detection will depend upon the chromophore released upon hydrolyis of the Asp-X bond. Fluorometric leaving groups (e.g. AMC) require spectrofluorometer such as the Gilford Fluoro IV. The emission and excitation wavelengths will be selected based on the emission and excitation spectra of the substrate and product chromophore. In the case of Ac-Tyr-Val-Ala-Asp-AMC, the excitation wavelength is 380 nm and the emission wavelength is 460nm.

Substrates with spectrophotometric leaving groups (eg. pNA) will require a spectrophotometer such as a CARY 210 spectrophotometer. In this case the reaction will be monitored at a wavelength whose selection will be based on the absorbance spectra of the substrate and product chromophore. In the case of Ac-Tyr-Val-Ala-Asp-PNA, the wavelength selected is 410 nm, although this can vary appreciably with only a minor compromise in the sensitivity of the assay.

In general, the fluorometric assays will be 10-fold more sensitive than spectrophotometric assays, consequently, the fluorometric assay is preferred if enzyme is precious. However, in the event that large quantities of active recombinant protein become available, the spectrophotometric assays are preferred. This assay is amenable to continuous or discontinuous sampling of the reaction. The assay is also amenable to 96-well plate format for running multiple assays simultaneously.

For example, with the fluorometric leaving group (e.g. AMC), the activity of the sample is proportional to the rate of fluorescence change, and be calculated as:

$$\text{Velocity of ICE Catalyzed reaction} = \frac{d\text{fluorescense}}{dt}\left(\frac{1\mu M\ AMC}{\text{fluorescence}}\right) = \frac{dAMC}{dt}$$

As appreciated by those of skill in the art, the use described above may be quite useful for determining Michaelis-Menton kinetic parameters or other characterization information concerning the Enzyme (eg when the sample contains no putatuve inhibitor) or screening for putative ICE inhibitors or assaying purification fractions.

In a fourth embodiment, the invention concerns a method of using a chromophore containing compound of formula II for determining the interleukin-1$\beta$ converting enzyme activity of a sample, comprising:

(a) adding, in aqueous solution, in any order, (1) a compound of formula II, (2) interleukin-1$\beta$ converting enzyme, (3) a sample, and (4) an aminopeptidase; and (b) measuring the interleukin-1$\beta$ converting enzyme activity of the product of step (a) by spectrophotometric or fluorometric analysis.

With the exception of the compound of Formula II and selection and concentration of components is the same as that stated for the third embodiment. With regard to the peptidase, any peptidase capable of cleaning the bond between $AA_4$ and $R_6$ will prove satisfactory.

Applicants have found a leucine aminopeptidase (LAPM) isolated from kidney microsomes (SIGMA CHEMICAL Co. No. L-0632) to be quite satisfactory.

It is not inherently essential that the sample and the LAPM be added at the same time. It is essential that the rate of hydrolysis by LAPM is not the rate limiting step of the overall reaction. We have found it useful to monitor the reaction continuously. The concentration of LAPM typically used in the assay is 1 $\mu$L, however, the amount used may vary widely (e.g. 0.01 units to 100 units per $\mu$l depending on the substitute and/or sample). [1 unit will hydrolyze 1.0 $\mu$mole of L-leucine-p-nitroaniline to leucine and p-nitroaniline per minute at pH 7.2 at 37° C.]

SCHEME I

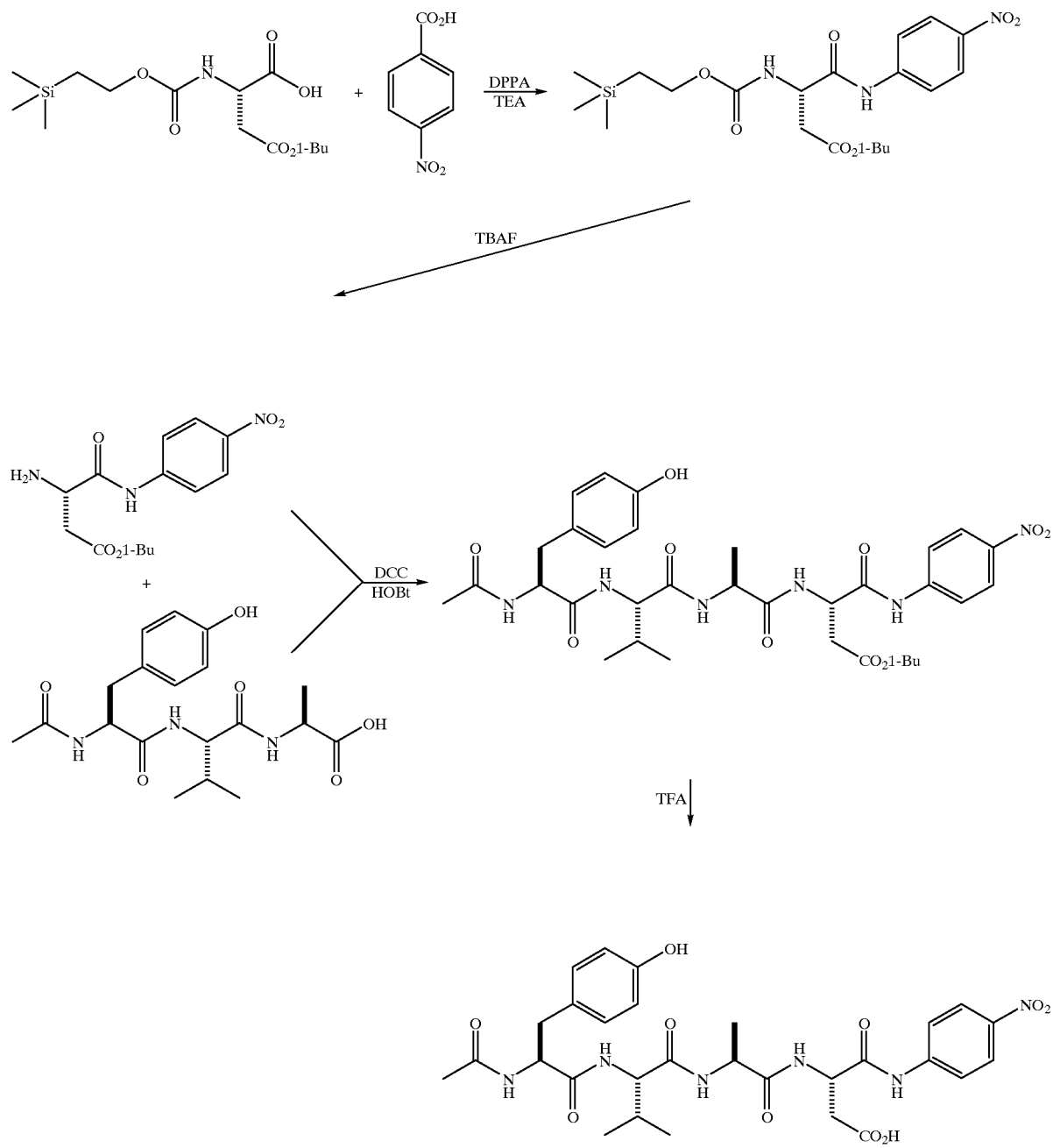

A chromophore can be coupled to a suitably protected aspartic acid derivative as shown in Scheme I. p-Nitrobenzoic acid is treated with DPPA in the presence of triethyl amine to effect a Curtius rearrangement. The resulting p-nitrophenylisocyanate reacts with N-trimethylsilylethyloxycarbonyl aspartic acid b-t-butyl ester to form the corresponding p-nitroanilide. The urethane is removed with tetrabutyl ammonium fluoride and the resulting amine coupled to (N-acetyl-tyrosinyl)-valinyl-aline using DCC and HOBt. The t-butyl ester is then removed with trifluoroacetic acid to provide the desired chromogenic peptide.

SCHEME II

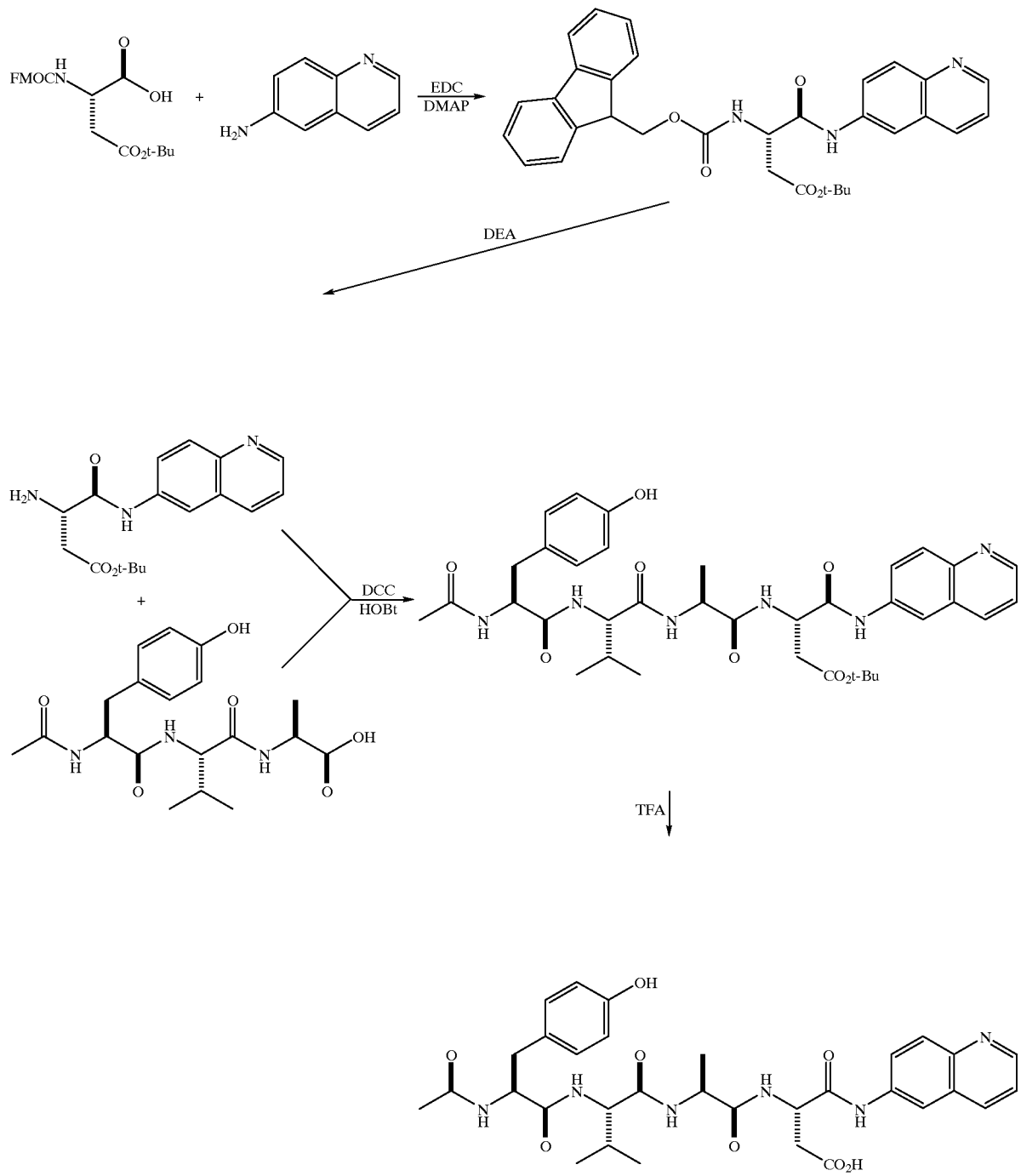

A chromophore can also be coupled to a suitably protected aspartic acid derivative as shown in Scheme II. 6-Aminoquinoline reacts with FMOC-aspartic acid B-t-butyl ester to form the corresponding amide in the presence of EDC and DMAP. The FMOC group is removed with diethyl amine and the resulting amine coupled to (N-acetyl-tyrosinyl)-valinyl-alanine using DCC and HOBt. The t-butyl ester is then removed with trifluoroacetic acid to provide the desired chromogenic peptide.

SCHEME III

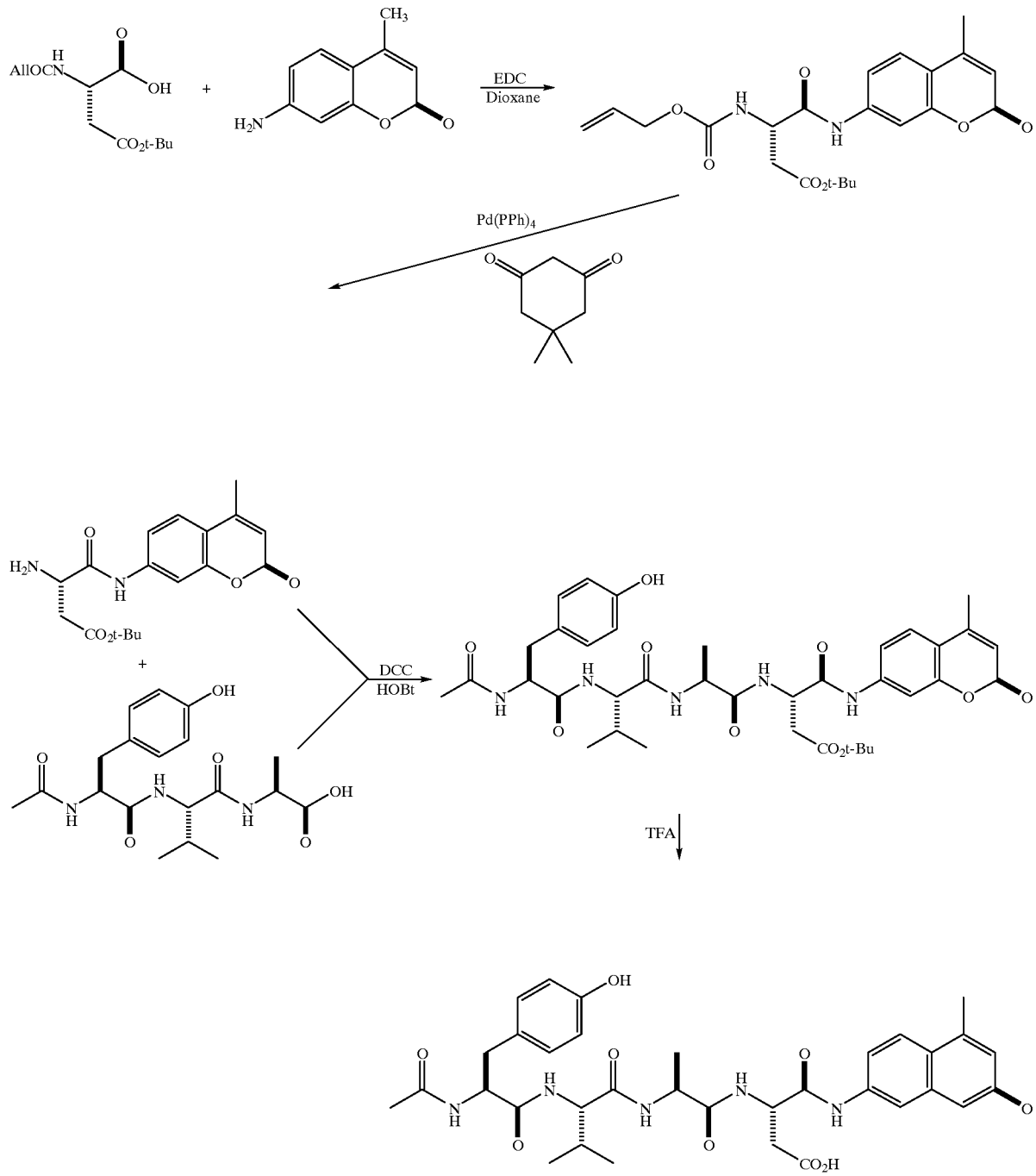

A chromophore can also be coupled to a suitably protected aspartic acid derivative as shown in Scheme III. 7-Amino-4-methylquinoline reacts with Alloc-aspartic acid B-t-butyl ester to form the corresponding amide in the presence of EDC. The Alloc group is removed with tetrakis triphenylphosphine palladium and dimedone and the resulting amines coupled to (N-acetyl-tyrosinyl)-valinyl-aline using DCC and HOBt. The t-butyl ester is then removed with trifluoroacetic acid to provide the desired chromogenic peptide.

SCHEME IV

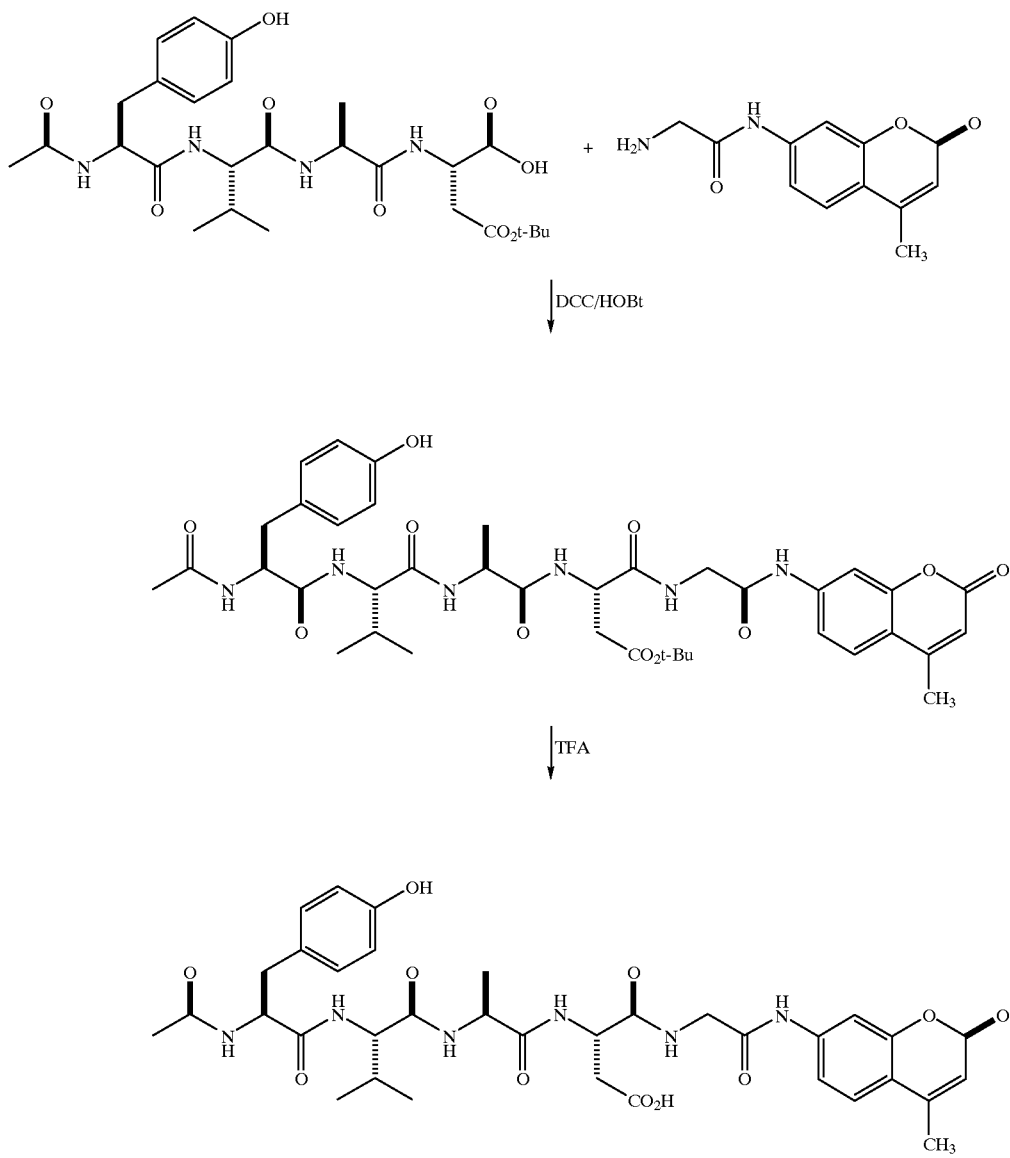

A chromogenic peptide substrate for IL-1B converting enzyme can also be prepared as shown in Scheme IV. (N-Acetyl-tyrosinyl)-valinyl-alaninyl-aspartic acid B-t-butyl ester can be coupled to commercially available glycine 7-amino-4-methylcoumarin amide using DCC and HOBt. The t-butyl ester is then removed with trifluoroacetic acid to provide the desired chromogenic peptide.

The following Examples are intended to illustrate the invention, and as such are not intended to limit the invention as set forth in the claims appended, thereto. The compounds of Formula I described in Examples 1A, 1B, 2, 6, 7 and 8 correspond to the peptide sequence which is SEQ. ID NO: 2:.

The compounds of Formula I described in Examples 3 and 5 correspond to the peptide sequence which is SEQ. ID NO: 3:.

EXAMPLE 1A

Direct Assay: Interleukin 1β activity of Activity of DEAE-purified THP-1 cell lysate.

| Enzyme: | THP-1 cell lysate purified approximately 100-fold using DEAE-anion exchange chromatography stock concentration = 5 units/ul (a unit is defined as the amount of enzyme required to produce 1 pmole of AMC/min at 25 degrees using saturating levels of substrate (>=50 μM). |
|---|---|
| Substrate: | N-(N-Acetyl-Tyrosinyl)-Valinyl-alaninyl-aspartic acid 7-amino-4-methylcoumarin |

| Buffer: | amide (i.e. Ac-Tyr-Val-Ala-Asp-AMC)<br>5 mM stock solution in DMSO<br>100 mM Hepes<br>10% sucrose<br>0.1% Chaps<br>1 mM DTT<br>1 mg/ml BSA<br>pH 7.5 |
|---|---|

At 25° C., 5 µl of substrate and 5 µl of enzyme was added to 490 µl of Buffer as defined above.

Liberation of 7-Amino-4-methylcoumarin (AMC) was monitored using a Gilford Fluoro IV Spectrofluorometer using an excitation wavelength of 380 nm and an emmission wavelength of 460 nm. 1 µM AMC =100% relative fluoroscence.

Results:

100% relative fluorescence achieved in 20 min (ie rate= 0.005 mM AMC/min.

EXAMPLE 1B

Direct Assay: Interleukin 1β activity of Activity of DEAE-purified THP-1 cell lysate in the presence of an enzyme inhibitor.

| Enzyme: | THP-1 cell lysate purified approximately 100-fold using DEAE-anion exchange chromatography<br>stock concentration = 5 units/ul<br>(a unit is defined as the amount of enzyme required to produce 1 pmole of AMC/min at 25 degrees using saturating levels of substrate (>=50 µM). |
|---|---|
| Substrate: | Ac-Tyr-Val-Ala-Asp-AMC<br>5 mM stock solution in DMSO |
| Buffer: | 100 mM Hepes<br>10% sucrose<br>0.1% Chaps<br>1 mM DTT<br>1 mg/ml BSA<br>pH 7.5 |
| Sample: | compound Z (i.e. N-(N-acetyl-tyrosinyl-valinyl-alaninyl)-3-amino-4-oxo butanoic acid)<br>2 µM in H₂O |

At 25° C., 5 µl of substrate 5 µl of enzyme and 5 µl of sample were added to 485 µl of Buffer as defined above.

Liberation of AMC was monitored using a Gilford Fluoro IV Spectrofluorometer using an excitation wavelength of 380 nm and an emmission wavelength of 460 nm. 1 µM AMC=100% relative fluorescence.

Results:

Compound Z is a slow, tight-binding inhibitor of the reaction. Consequently, the continuous output from the fluorometer reveals as uninhibited initial velocity, and the slow onset of inhibition which eventually approaches 100%. The initial velocity is 0.05 uM AMC produced/min, and the rate constant for inhibition is 0.25 min$^{-1}$, corresponding to a half-life for the slow onset of inhibition of 2.7 min.

EXAMPLE 2

Direct Assay: Interleukin 1β activity of Activity of DEAE-purified THP-1 cell lysate.

| Enzyme: | THP-1 cell lysate purified approximately 100-fold using DEAE-anion exchange chromatography<br>stock concentration = 5 units/ul<br>(a unit is defined as the amount of enzyme required to produce 1 pmole of p-NA/min at 25 degrees using saturating levels of substrate. p-NA is para-nitroanaline. |
|---|---|
| Substrate: | Ac-Tyr-Val-Ala-Asp-p-NA<br>5 mM stock solution in DMSO |
| Buffer: | 100 mM Hepes<br>10% sucrose<br>0.1% Chaps<br>1 mM DTT<br>1 mg/ml BSA<br>pH 7.5 |

At 25° C., 5 ml of substrate and 5 ml of enzyme was added to 490 ml of Buffer as defined above.

Reaction is monitored continuously in a Cary 219 spectrophotometer at a wavelength of 410 nm.

Results: The rate of the reaction under these conditions is 0.005 absorbance units/min, corresponding to 0.5 uM pNA produced/min.

EXAMPLE 3

Coupled Assay: Interleukin 1β activity of

Activity of DEAE-purified THP-1 cell lysate.

| Enzyme: | THP-1 cell lysate purified approximately 100-fold using DEAE-anion exchange chromatography<br>stock concentration = 5 units/ul<br>(a unit is defined as the amount of enzyme required to produce 1 pmole of AMC/min at 25 degrees using saturating levels of substrate (=50 uM). |
|---|---|

Coupling

| Enzyme: | Leucine Aminopetidase Microsomal (Type IV) (LAPM) (purified from porcine kidney microsomes)<br>EC 3.4.11.2<br>Sigma No. L-0632<br>12.5 units/ml stock solution in DMSO |
|---|---|
| Substrate: | Ac-Tyr-Val-Ala-Asp-Gly-AMC<br>5 mM stock solution in DMSO |
| Buffer: | 100 mM Hepes<br>10% sucrose<br>0.1% Chaps<br>1 mM DTT<br>1 mg/ml BSA<br>pH 7.5 |

At 25° C., 5 µl of substrate 5 µl of LAPM, 5 µl of ICE were added to 440µl of buffer.

Reaction is monitored continuously in a Gilford Fluoro-IV Spectrofluorometer.

excitation wavelength=380 nm emission wavelength=460 nm 1 uM AMC=100% relative fluoroescence Results: A lag phase appears prior to attainment of a steady state velocity. The rate constant that describes the approach to steady state (0.44+0.01 min−1) is determined by the amount of coupling enzyme present in the reaction, and the steady state velocity is a measure of the reaction catalyzed by ICE.

Consequently, 11 min (7×t ½) are required to reach 99% of the steady state of the ICE reaction. The velocity of the steady state reaction is 0.05 uM AMC/min.

EXAMPLE 4

Step A: Cell Growth:

THP.1 cells obtained from the ATCC (accession number ATCC TIB202) were grown in suspension in ISCOVE's MODIFIED DULBECCO's Medium or in DULBECCO's MODIFIED EAGLES MEDIUM (JRH BIOSCIENCES) with 9% horse serum in either roller bottles, WHEATON TURBOLIFT 46 liter suspension flasks, or in 75, 200, or 300 liter fermenters with weekly harvests at 1–2×10$_6$ cells/ml (3–4 doublings/week). Media used in suspension flasks or fermenters also contained 0.1–0.3% F68 pluronic to reduce shear force on the cells. Cells were typically grown for no more than 3–4 months following initial startup from the ATCC vial.

Step B: Cell Breakage and Fractionation:

Cells were washed 3 times in PBS and suspended 20 minutes at 0° C. at 10$^8$ cells/ml in a hypotonic buffer containing 25 mM HEPES, pH 7.5, 5 mM MgCl$_2$, and 1 mM EGTA. Protease inhibitors were added (1 mM PMSF and 10 μg/ml of pepstatin and leupeptin), and the cells were broken in 100 or 300 ml tight fitting DOUNCE homogenizers using 25 or 15 strokes respectively to yield 90–95% breakage. The broken cells were centrifuged at 3000 rpm, 10 minutes, 5° C. in a BECKMAN GPR centrifuge to remove nuclei and unbroken cells. The resultant pellet was resuspended in about ¼ the original volume of the hypotonic buffer with the protease inhibitors, and the suspension was rebounded for 10 strokes and recentrifuged. This second postnuclear supernatant was added to the first.

The postnuclear supernatant was centrifuged for 20 minutes, 16,000 rpm in a SORVAL centrifuge with an SS34 rotor followed by a second spin for 60 minutes at 50,000 rpm in a BECKMAN centrifuge (50.2Ti rotor) or 45,000 rpm (45Ti rotor). After addition of 2 mM DTT, the resultant supernatant was stored at −80° C. until purification of ICE.

Step C: HPLC Column Purification of ICE:

The thawed supernatants were clarified by 0.22 μ hollow fiber filtration and concentrated 10–20 fold with an AMICON YM3 spiral cartridge and dialyzed overnight (8000 molecular weight cutoff dialysis membrane) vs a buffer of 20 mM Tris, pH 7.8, 10% sucrose, 0.1% CHAPS, and 2 mM DTT. The dialyzed supernatant (ca. 3–5 g total protein, corresponding to 1000 ml of cytosolic extract) was adjusted to less than 500 MICROSIEMANS conductivity with water and applied to a 475 ml bed volume DEAE-5PW HPLC (BIORAD) column. ICE was eluted at about 40 mM NaCl in a gradient with the same buffer and increasing proportions of 0.5 M NaCl and 220 mM Tris HCl. The ICE active fractions were assayed using a 96 well plate fluorometric assay with a 100 μl volume containing 100 μM YVAD-AMC substrate in a buffer of 25 mM HEPES, pH 7.5, 10% sucrose, 0.1% CHAPS, and 2 mM DTT.

EXAMPLE 5

N-(N-Acetyl-tyrosinyl-valinyl-alaninyl-aspartyl-glycinyl)-7-amino-4-methylcoumarin.

Step A:

N-(N-Acetyl-tyrosinyl-valinyl-alaninyl-(aspartyl-b-t-butyl ester)-glycinyl)-7-amino-4-methylcoumarin.

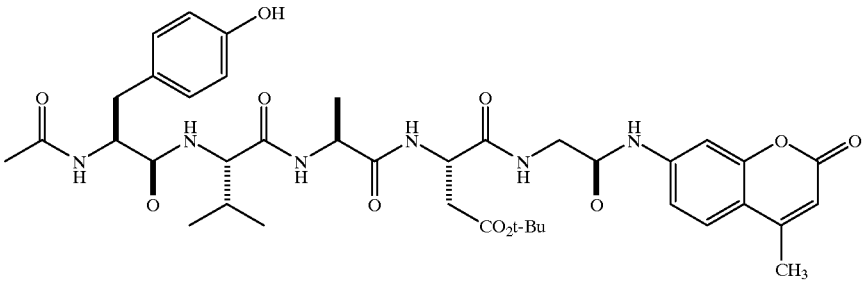

To a solution of N-Acetyl-tyrosinyl-valinyl-alaninyl-aspartic acid b-t-butyl ester (100 mg, 0.163 mmol) in 2 mL of DMF at 0° C. was added N-(glycinyl)-7-amino-4-methylcoumarin (41.7 mg, 0.18 mmol), hydroxybenzotriazole (66 mg, 0.489 mmol), and dicyclohexylcarbodiimide (67 mg, 0.326 mmol). After 24 hours at ambient temperature, the mixture was filtered and purified by Sephadex" LH-20 chromatography (1M×50 mm column, methanol eluent). The resulting product was further purified by MPLC on silica-gel (22×300 mm column, eluting with a linear gradient of dichloromethane to 10% methanol in dichloromethane) to give the title compound as a colorless solid: $^1$H NMR (200 MHz, DMF-d$_7$) d 8.5–7.6 (m, 10H), 7.1 (br d, 2H), 6.75 (br d, 2H), 6.3 (q, 1H, J=1 Hz), 4.8–3.9 (m, 6H), 3.1–2.7 (m, 4H), 2.48 (d, 3H, J=1 Hz), 2.1 (m, 1H), 1.9 (s, 3H), 1.44 (s, 9H), 1.41 (d, 3H, J=7.3 Hz), 0.93 (d, 3H, J=6.7 Hz), 0.91 (d, 3H, J=6.7 Hz).

Step B:

N-(N-Acetyl-tyrosinyl-valinyl-alaninyl-aspartyl-glycinyl)-7-amino-4-methylcoumarin.

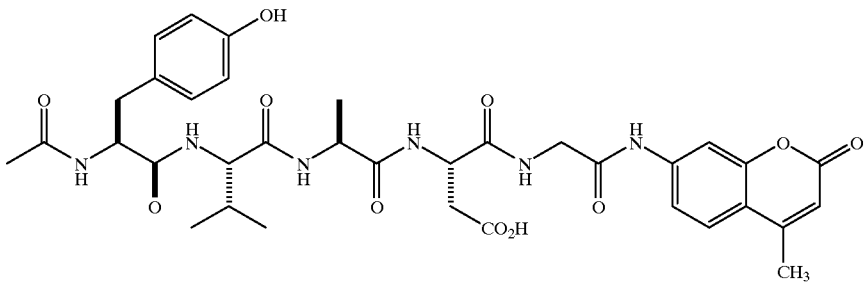

N-(N-Acetyl-tyrosinyl-valinyl-alaninyl-(aspartyl-b-t-b utyl ester)-glycinyl)-7-amino-4-methylcoumarin was disolved in trifluoroacetic acid and aged for 20 min. The mixture was concentrated in vacuo. The resulting solid was suspended in methanol and concentrated in vacuo and this procedure repeated to give the title compound as a colorless solid: $^1$H NMR (200 MHz, DMF-$d_7$) d 8.5–7.6 (m, 10H), 7.1 (br d, 2H), 6.75 (br d, 2H), 6.3 (q, 1H, J=1 Hz), 4.8–3.9 (m, 6H), 3.2–2.7 (m, 4H), 2.48 (d, 3H, J=1 Hz), 2.12 (m, 1H), 1.9 (s, 3H), 1.41 (d, 3H, J=7 Hz), 0.93 (d, 3H, J=6.5 Hz), 0.91 (d, 3H, J=6.5 Hz).

EXAMPLE 6

N-(N-Acetyl-tyrosinyl-valinyl-alaninyl-aspartic acid p-nitroanilide.

Step A:

N-(2-Trimethylsilylethyloxycarbonyl)-aspartic acid b-t-butyl ester p-nitroanilide.

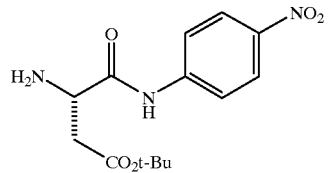

To a solution of p-nitrobenzoic acid (1.45 g, 8.69 mmol) and triethyl amine (1.21 mL, 8.69 mmol) in 10 mL of 1,2-dichloroethane was added diphenylphosphoryl azide (2.39 g, 8.69 mmol). After 2 h at ambient temperature and 15 min at reflux, a solution of N-(2-Trimethylsilylethyloxycarbonyl)-aspartic acid b-t-butyl ester (1.45 g, 4.35 mmol) in 15 mL of 1,2-dichloroethane was added and the mixture refluxed for 1 h. The mixture was cooled, concentrated in vacuo, disolved in 500 mL of 4:1 ethyl acetate:benzene and washed with 1 N citric acid, water, saturated sodium bicarbonate, water, and brine. The mixture was dried over sodium sulfate and concentrated in vacuo. The mixture was triturated with ethyl acetate and the solid discarded. The solution was concentrated and purified by MPLC on silica-gel (35×300 mm column, 20% ethyl acetate/hexane as eluent) to give the title compound as a colorless solid: $^1$H NMR (200 MHz, CDCl$_3$) d 9.05 (br s, 1H), 8.18 (dt, 2H, J=2.33, 9.21 Hz), 7.68 (dt, 2H, J=2.29, 9.21 Hz), 5.92 (br d, 1H), 4.63 (m, 1H), 4.21 (m, 2H), 2.95 (dd, 1J, J=4.13,17.15 Hz), 2.68 (dd, 1H, J=6.56, 17.07 Hz), 1.44 (s, 9H), 0,99 (m, 2H), 0.03 (s, 9H).

Step B:

Aspartic acid b-t-butyl ester p-nitroanilide.

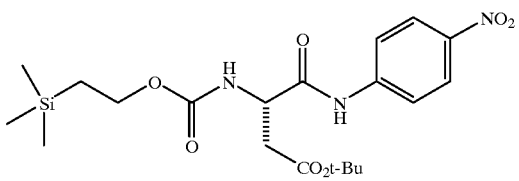

To a solution of N-(2-Trimethylsilylethyloxy-carbonyl)-aspartic acid b-t-butyl ester p-nitroanilide (536 mg, 1.24 mmol) in 2.5 mL of acetonitrile was added 2.48 mL of a solution of tetrabutyl ammonium fluoride in tetrahydrofuran (2.48 mmol). The mixture was held at 50° C. for 16 h then poured into ethyl acetate. The mixture was extracted with three portions of 1 N hydrochloric acid and the combined aqueous layers bascified with saturated sodium bicarbonate and extracted with ethyl acetate. The organic layer was washed twice with saturated sodium bicarbonate and twice with water then dried over sodium sulfate and concentrated. The mixture was purified by MPLC on silica-gel (35×300 mm column, eluting with a gradient of dichloromethane to 0.5% ammonia and 5% methanol in dichloromethane) to give the title compound as a pale-orange solid: $^1$H NMR (200 MHz, CD$_3$OD) d 8.21 (dt, 2H, J=1.69, 9.13 Hz), 7.85 (dt, 2H, J=2.22, 9.02 Hz), 3.77 (t, 1H, J=6.14 Hz), 2.76 (dd, 1H, J=6.07,16.72 Hz), 2.63 (dd, 1H, J=6.17, 16.12 Hz), 1.42 (s, 9H).

Step C:

N-(N-Acetyl-tyrosinyl-valinyl-alaninyl-aspartic acid b-t-butyl ester p-nitroanilide.

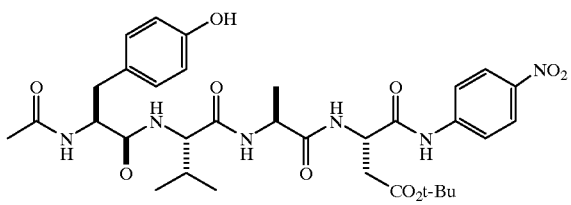

To a solution of N-(N-Acetyl-tyrosinyl-valinyl-alanine benzyl ester (106 mg, 0.219 mmol) in 3 mL of methanol was added 10 mg of Pearlman's catalyst (Pd(OH)$_2$ on carbon). After 2 h under an atmosphere of hydrogen, the mixture was filtered and concentrated. Aspartic acid b-t-butyl ester p-nitroanilide (81.4 mg, 0.263 mmol) was added followed by hydroxybenzotriazole (89 mg, 0.66 mmol) and 2 mL of dimethyl formamide. The mixture was cooled to 0° C. and dicyclohexylcarbodiimide (90 mg, 0.438) was added. After 16 h at ambient temperature, the mixture was filtered and purified by Sephadex" LH-20 chromatography (1M×50 mm column, methanol eluent). The resulting product was further purified by MPLC on silica-gel (22×300 mm column, eluting with a linear gradient of dichloromethane to 20% methanol in dichloromethane) to give the title compound as a colorless solid: $^1$H NMR (200 MHz, DMF-$d_7$) d 8.3–7.9 (m, 9H), 7.09 (br d, 2H, J=8.64 Hz), 6.73 (br d, 2H, J=8.61 Hz), 4.82 (br q, 1H, J=6.03 Hz), 4.6 (m, 1H), 4.4–4.15 (m, 2H), 3.1–2.7 (m, 4H), 2.1 (m, 1H), 1.87 (s, 3H), 1.43 (d, 1.5H, J=6.88 Hz), 1.41 (s, 9H), 1.37 (d, 1.5H, J=6.88 Hz), 0.92 (d, 3H, J=6.60 Hz), 0.91 (d, 3H, J=6.12 Hz).

Step D:

N-(N-Acetyl-tyrosinyl-valinyl-alaninyl-aspartic acid p-nitroanilide.

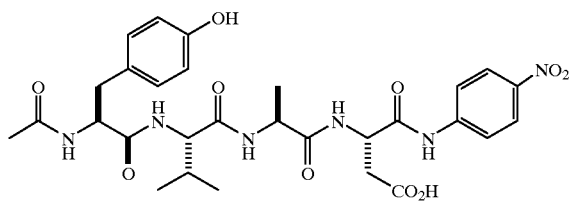

N-(N-Acetyl-tyrosinyl-valinyl-alaninyl-aspartic acid b-t-butyl ester p-nitroanilide (138.9 mg) was disolved in 6 mL of trifluoroacetic acid. After 15 min, the mixture was concentrated, then diluted with methanol and concentrated several times. The mixture was purified by MPLC on silica-gel (22×300 mm column, eluting with a linear gradient of 0.2% TFA in dichloromethane to 0.2% TFA and 20% methanol in dichloromethane) then further purified by Sephadex" LH-20 chromatography (1M ×25 mm column, methanol eluent). The resulting product was triturated with ether to give the title compound as a colorless solid: $^1$H NMR (200 MHz, CD$_3$OD) d 8.17 (dt, 2H, J=2.26, 9.06 Hz), 7.88 (dt, 2H, J=2.15, 9.06 Hz), 7.01 (br d, 2H), 6.65 (br d, 2H), 4.75 (m, 1H), 4.52 (m, 1H), 4.3–4.0 (m, 3H), 3.0–2.6 (m, 4H), 1.98 (m, 1H), 1.88 (s, 3H), 1.35 (d, 3H, J=6.81 Hz), 0.89 (d, 6H, J=7.05 Hz).

EXAMPLE 7

N-(N-Acetyl-tyrosinyl-valinyl-alaninyl-aspartic acid a-6-aminoquin-oline amide.

Step A: N-(9-Florenylmethyloxycarbonyl)-aspartic acid b-t-butyl ester a-6-aminoquinoline amide.

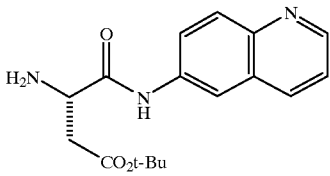

To a solution of N-(9-Florenylmethyloxycarbonyl)-aspartic acid b-t-butyl ester (1.00 g, 2.43 mmol), 6-aminoquinoline (385 mg, 2.67 mmol), and 20 mg of dimethylaminopyridine in 10 mL of dichloromethane at 0° C. was added ethyl dimethylaminopropyl carbodiimide (699 mg, 3.65 mmol). After 1.5 h at 0° C., the mixture was diluted with ethyl acetate and washed three times with saturated sodium bicarbonate and three times with water, then dried over sodium sulfate and concentrated. The mixture was then purified by MPLC on silica-gel (35×300 mm column, 50% ethyl acetate/dichloromethane as eluent) to give the title compound as a colorless foam: $^1$H NMR (200 MHz, CDCl$_3$) d 8.8 (m, 2H), 8.26 (d, 1H), 8.08 (br d, 1H), 8.04 (d, 1H), 7.75 (d, 1H), 7.58 (m, 3H), 7.45–7.2 (m, 6H), 6.1 (br s, 1H), 4.7 (br s, 1H), 4.52 (d, 2H), 4.24 (t, 1H), 2.98 (dd, 1H), 2.70 (dd, 1H), 1.47 (s, 9H).

Step B:

Aspartic acid b-t-butyl ester a-6-aminoquinoline amide.

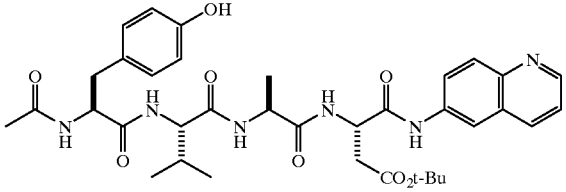

To a solution of N-(9-Florenylmethyloxycarbonyl)-aspartic acid b-t-butyl ester a-6-aminoquinoline amide in 20 mL of acetonitrile was added 20 mL of diethyl amine. After 1h at ambient temperature, the mixture was concentrated and purified by MPLC on silica-gel (35×300 mm column, eluting with a gradient of dichloromethane to 1% ammonia and 10% methanol in dichloromethane) to give the title compound: $^1$H NMR (200 MHz, CD$_3$OD) d 8.73 (dd, 2H, J=1.52, 3.92 Hz), 8.37 (d, 1H, J=2.68 Hz), 8.27 (br d, 1H, J=8.11 Hz), 7.97 (d, 1H, J=9.24 Hz), 7.84 (dd, 1H, J=2.12, 8.68), 7.49 (dd, 1H, J=4.55, 8.18 Hz), 3.81 (dd, 1H, J=6.10, 7.30 Hz), 2.79 (dd, 1H, J=6.24, 16.19 Hz), 2.66 (dd, 1H, J=6.63, 16.19 Hz), 1.43 (s, 9H).

Step C:

N-(N-Acetyl-tyrosinyl-valinyl-alaninyl-aspartic acid b-t-butyl ester a-6-aminoquinoline aside.

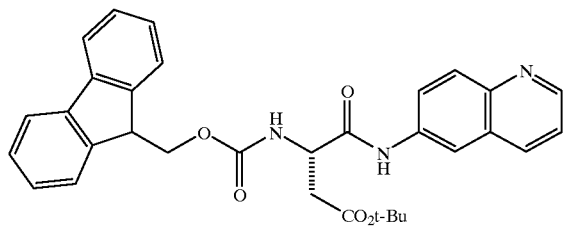

To a solution of N-(N-Acetyl-tyrosinyl-valinyl-alanine benzyl ester (102 mg, 0.211 mmol) in 3 mL of methanol was added 10 mg of Pearlman's catalyst (Pd(OH)$_2$ on carbon). After 2 h under an atmosphere of hydrogen, the mixture was filtered and concentrated. Aspartic acid b-t-butyl ester a-6-aminoquinoline amide (100 mg, 0.32 mmol) was added followed by hydroxybenzotriazole (57 mg, 0.42 mmol) and 2 mL of dimethyl formamide. The mixture was cooled to 0° C. and dicyclohexylcarbodiimide (65 mg, 0.316) was added. After 16 h at ambient temperature, the mixture was filtered and purified by Sephadex" LH-20 chromatography (1M×50 mm column, methanol eluent). The resulting product was further purified by MPLC on silica-gel (22×300 mm column, eluting with a linear gradient of dichloromethane to 2% ammonia and 20% methanol in dichloromethane) to give the title compound as a colorless solid: ¹H NMR (200 MHz, DMF-d₇) d 8.82 (dd, 2H, J=1.48, 4.06 Hz), 8.53 (d, 1H, J=1.90 Hz), 8.32 (m, 3H), 8.2–8.0 (m, 5H), 7.49 (dd, 1H, J=4.02, 8.18 Hz), 7.09 (br d, 2H, J=8.64 Hz), 6.73 (br d, 2H, J=8.00 Hz), 4.87 (br q, 1H, J=6.03 Hz), 4.65 (m, 1H), 4.5–4.2 (m, 2H), 3.2–2.8 (m, 4H), 2.18 (m, 1H), 1.87 (s, 3H), 1.41 (s, 9H), 1.38 (d, 3H, J=6.95 Hz), 0.94 (d, 6H, J=6.34 Hz).

Step D:

N-(N-Acetyl-tyrosinyl-valinyl-alaninyl-aspartic acid a-6-aminoquin-oline aside.

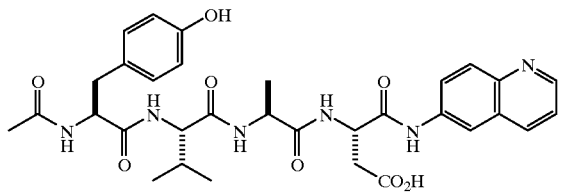

N-(N-Acetyl-tyrosinyl-valinyl-alaninyl-aspartic acid b-t-butyl ester a-6-aminoquinoline amide was disolved in trifluoroacetic acid and held for 15 min. The mixture was then concentrated, diluted with methanol and toluene and concentrated severel times to give the title compound as a colorless solid: ¹H NMR (200 MHz, DMF-d₇) d 8.99 (br d 1H, J=5.01 Hz), 8.92 (br d, 1H, J=8.18 Hz), 8.74 (d, 1H, J=2.22 Hz), 8.29 (dd, 1H, J=2.15, 9.14 Hz), 8.12 (d, 1H, 9.13 Hz), 7.93 (dd, 1H, J=5.47, 8.11 Hz), 7.02 (br d, 2H, J=8.57 Hz), 6.64 (br d, 2H, J=8.57 Hz), 4.8 (m, 1H), 4.56 (dd, 1H, J=5.96, 8.50 Hz), 4.26 (m, 1H), 4.12 (m, 1H), 3.12–2.7 (m, 4H), 2.05 (m, 1H), 1.90 (s, 3H), 1.40 (d, 3H, J=6.81 Hz), 0.91 (d, 6H, J=6.67 Hz).

EXAMPLE 8

N-(N-Acetyl-tyrosinyl-valinyl-alaninyl)-aspartic acid a-7-amino-4-methylcoumarin amide.

Step A:

N-Allyloxycarbonyl aspartic acid b-t-butyl ester a-7-amino-4-methylcoumarin amide.

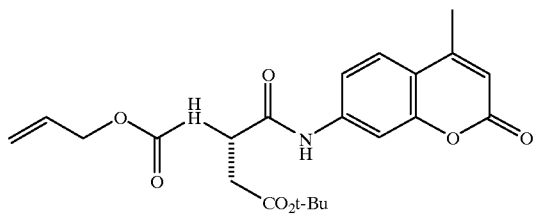

To a solution of N-alylloxycarbonyl aspartic acid b-t-butyl ester (3.44g, (12.6 mmol) and 7-amin-4-methylcoumarin (2.00 g, 11.42 mmol) in 15 mL of anhydrous dioxane was added ethyl dimethylaminopropyl carbodiimide (2.66 g, 13.86 mmol). After 75 min at reflux, the mixtuire was diluted with ethyl acetate and washed three times with 1 N hydrochloric acid and three times with saturated sodium bicarbonate. The solution was dried over sodium sulfate and concentrated in vacuo. The mixture was purified by MPLC on silica-gel (35×300 mm column, 10% ethyl acetate in dichloromethane as eluent) to give the title compound as a colorless foam: ¹H NMR (200 MHz, CD₃OD) d 7.77 (d, 1H, J=2.39 Hz), 7.68 (d, 1H, J=9.06 Hz), 7.49 (dd, 1H, J=2.36, 9.10 Hz), 6.21 (q, 1H, J=1.30 Hz), 5.95 (m, 1H), 5.4–5.15 (m, 2H), 4.72–4.58 (m, 3H), 2.85 (dd, 1H, J=6.17, 15.73 Hz), 2.65 (dd, 1H, J=7.62, 16.37 Hz), 2.43 (d, 3H, J=1.44 Hz), 1.43 (s, 9H).

Step B:

Aspartic acid b-t-butyl ester a-7-amino-4-methylcoumarin amide.

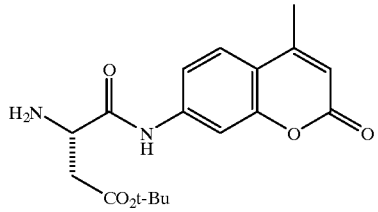

To a solution of N-Allyloxycarbonyl aspartic acid b-t-butyl ester a-7-amino-4-methylcoumarin amide (435 mg, 1.01 mmol) and Dimedone (1.13 g, 8.08 mmol) in 10 mL of anhydrous tetrahydrofuran was added tetrakis triphenylphosphine palladium (117 mg, 0.1 mmol). After 45 min, the mixtuire was diluted with ethyl acetate and washed five times with saturated sodium bicarbonate, dried over sodium sulfate and concentrated in vacuo. The mixture was disolved in a small amount of a solution of 1% ammonia and 10% methanol in dichloromethane and filtered through a 0.22 mm filter. The mixture was then purified by MPLC on silica-gel (22×300 mm column, eluting with a gradient of dichloromethane to 0.25% ammonia and 2.5% methanol in dichloromethane) to give the title compound as a colorless foam: ¹H NMR (200 MHz, CD₃OD) d 7.93 (d, 1H, J=1.76 Hz), 7.82 (d, 1H, J=8.50 Hz), 7.63 (dd, 1H, J=2.40, 9.10 Hz), 6.34 (q, 1H, J=1.31 Hz), 3.89 (t, 1H, J=6.35 Hz), 2.88 (dd, 1H, J=6.03, 16.72 Hz), 2.75 (dd, 1H, J=6.77, 16.75 Hz), 2.56 (d, 3H, J=1.37 Hz), 1.54 (s, 9H).

Step C:

N-(N-Acetyl-tyrosinyl-valinyl-alaninyl)-aspartic acid b-t-butyl ester a-7-amino-4-methylcoumarin.

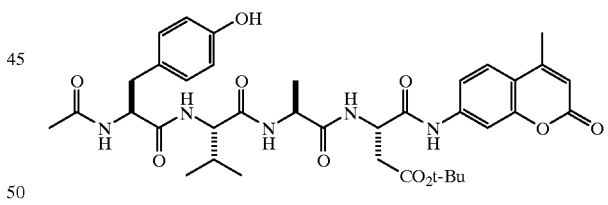

To a solution of N-(N-Acetyl-tyrosinyl-valinyl-alanine (288 mg, 0.733 mmol), aspartic acid b-t-butyl ester a-7-amino-4-methylcoumarin (242 mg, 0.698 mmol) and hydroxybenzotriazole (149 mg, 1.10 mmol) in 2 mL of dimethyl formamide at 0° C. was added dicyclohexylcarbodiimide (151 mg, 0.733). After 16 h at ambient temperature, the mixture was filtered and purified by Sephadex" LH-20 chromatography (1M×50 mm column, methanol eluent). The resulting product was triturated with methanol to give the title compound as a colorless solid: ¹H NMR (200 MHz, DMF-d₇) d 8.3–7.5 (m, 7H), 7.09 (br d, 2H, J=8.61 Hz), 6.72 (br d, 2H, J=8.64 Hz), 6.27 (q, 1H, J=1.31 Hz), 4.84 (m, 1H), 4.62 (m, 1H), 4.44–4.14 (m, 2H), 3.15–2.7 (m, 4H), 2.45 (d, 3H, J=1.37 Hz), 2.13 (m, 1H), 1.87 (s, 3H), 1.41 (s, 9H), 1.37 (d, 3H. J=7.38 Hz), 0.94 (d, 3H, J=7.12 Hz), 0.93 (d, 3H, J=7.12 Hz).

Step D:

N-(N-Acetyl-tyrosinyl-valinyl-alaninyl)-aspartic acid a-7-amuino-4-methylcoumarin amide.

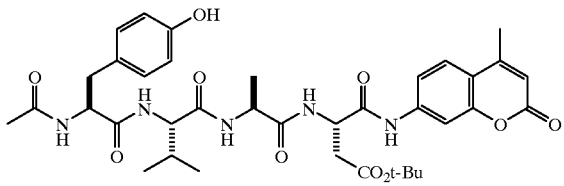

N-(N-Acetyl-tyrosinyl-valinyl-alaninyl)-aspartic acid b-t-butyl ester a-7-amino-4-methylcoumarin amide was dissolved in trifluoroacetic acid. After 15 min the mixture was concentrated in vacuo to give the title compound as a colorless solid: $^1$H NMR (200 MHz, DMF-$d_7$) d 8.3–7.5 (m, 7H), 7.09 (br d, 2H, J=8.61 Hz), 6.72 (br d, 2H, J=8.64 Hz), 6.27 (q, 1H, J=1.31 Hz), 4.84 (m, 1H), 4.62 (m, 1H), 4.44–4.14 (m, 2H), 3.15–2.7 (m, 4H), 2.45 (d, 3H, J=1.37 Hz), 2.13 (m, 1H), 1.87 (s, 3H), 1.41 (s, 9H), 1.37 (d, 3H. J=7.38 Hz), 0.94 (d, 3H, J=7.12 Hz), 0.93 (d, 3H, J=7.12 Hz). Microanalysis calculated for $C_{33}H_{39}N_5O_{10} \cdot 1.65\ H_2O$: C, 57.00, H, 6.13, N, 10.07; found: C, 56.97, H, 5.84, N 10.16.

---

What is claimed is:

1. A compound of formula I

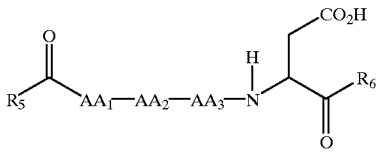

wherein $AA_1$ is an amino acid of formula AI

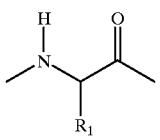

wherein $R_1$ is aryl $C_{1-6}$ alkyl wherein aryl is selected from the group consisting of
(1) phenyl,
(2) naphthyl,
(5) thienyl, and
(9) benzothienyl, wherein the aryl may be optionally substituted with hydroxy;

$AA_2$ is an amino acid of formula AII

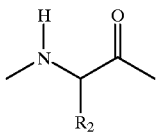

$AA_3$ is an amino acid of formula AIII

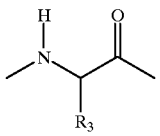

wherein $R_2$ and $R_3$ are each independently selected from the group consisting of
(a) hydrogen,
(b) substituted $C_{1-6}$alkyl, wherein the substituent is selected from
  (1) hydrogen,
  (2) hydroxy,
  (3) carboxy, (4)

(5) $C_{1-4}$ alkylamino, and $C_{1-4}$ alkyl amino wherein the alkyl moiety is substituted with an hydroxy, and (6) guanidino,
(11) amino, and
(c) aryl $C_{1-3}$ alkyl,
wherein aryl is defined as
(1) phenyl,
(2) naphthyl,
(3) thienyl,
(4) thiazolyl, and
(5) benzothienyl, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;

$R_6$ is selected from the group consisting of:
(a) mono or di substituted Aryl amino,
(b) mono or di substituted Aryl oxy, and
(c) mono or di substituted Aryl thio,
wherein the aryl group is selected from the group consisting of:

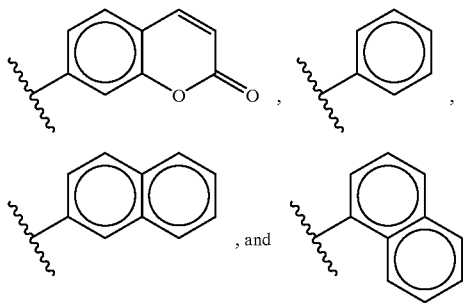

, and wherein the substituent is selected from the group consisting of
(1) H,
(2) OH,
(3) $C_{1-3}$alkyl,
(4) $C_{1-3}$alkyloxy,
(5) $CO_2H$,
(6) formyl, and
(7) CN.

2. A compound according to claim 1 wherein $R_5$ is methyl;
$R_2$ is $C_{1-6}$alkyl; and
$R_3$ is
(a) hydrogen,
(b) $C_{1-6}$alkyl,
(c) N-carbopenzoxy-amino-(n-butyl),
(c) indol-2-yl-methyl, or
(d) substituted phenyl $C_{1-3}$alkyl, wherein the substituent is hydrogen or hydroxy.

3. A method of using a compound of claim 2 for determining the interleukin-1β converting enzyme activity of a sample, comprising:
(a) adding, in aqueous solution, in any order,
  (1) a compound of formula I,
  (2) interleukin-1β converting enzyme, and
  (3) a sample; and
(b) measuring the interleukin-1β converting enzyme activity of the product of step (a) by spectrophotometric or fluorometric means.

4. A method of using a compound of claim 1 for determining the interleukin-1β converting enzyme activity of a sample, comprising:

(a) adding, in aqueous solution, in any order,
  (1) a compound of formula I,
  (2) interleukin-1β converting enzyme, and
  (3) a sample; and
(b) measuring the interleukin-1β converting enzyme activity of the product of step (a) by spectrophotometric or fluorometric means.

5. A compound selected from the group consisting of:
(a) (N-Acetyl-tyrosinyl)-valinyl-alaninyl-aspartic acid p-nitroanilide;
(b) (N-Acetyl-tyrosinyl)-valinyl-alaninyl-aspartic acid 6-aminoquinoline amide; and
(c) N-((N-Acetyl-tyrosinyl)-valinyl-alaninyl)-aspartic acid α-7-amino-4-methylcoumarin amide.

6. A method of using a compound of claim 5 for determining the interleukin-1β converting enzyme activity of a sample, comprising:
(a) adding, in aqueous solution, in any order,
  (1) a compound of formula I,
  (2) interleukin-1β converting enzyme, and
  (3) a sample; and
(b) measuring the interleukin-1β converting enzyme activity of the product of step (a) by spectrophotometric or fluorometric means.

7. A compound which is N-((N-Acetyl-tyrosinyl)-valinyl-alaninyl)-aspartic acid α-7-amino-4-methylcoumarin amide.

8. A method of using a compound of claim 7 for determining the interleukin-1β converting enzyme activity of a sample, comprising:
(a) adding, in aqueous solution, in any order,
  (1) a compound of formula I,
  (2) interleukin-1β converting enzyme, and
  (3) a sample; and
(b) measuring the interleukin-1β converting enzyme activity of the product of step (a) by spectrophotometric or fluorometric means.

9. A compound of formula I

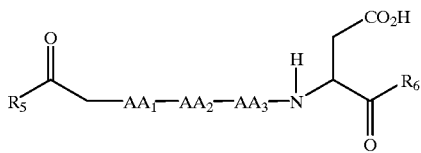

wherein
AA$_1$ is an amino acid of formula AI

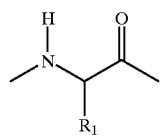

wherein
R$_1$ is an optionally monosubstituted aryl C$_{1-6}$ alkyl wherein aryl is selected from the group consisting of
  (1) phenyl,
  (2) naphthyl,
  (3) pyridyl,
  (4) furyl,
  (5) thienyl,
  (6) thiazolyl,
  (7) isothiazolyl,
  (8) benzofuryl,
  (9) benzothienyl,
  (10) indolyl,
  (11) isoxazolyl, and
  (12) oxazolyl, AA$_2$ is an amino acid of formula AII

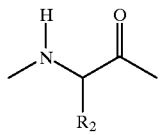

AA$_3$ is an amino acid of formula AIII

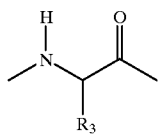

wherein R$_2$ and R$_3$ are each independently selected from the group consisting of
(a) hydrogen,
(b) substituted C$_{1-6}$alkyl, wherein the substituent is selected from
  (1) hydrogen,
  (2) hydroxy,
  (3) carboxy,

(4)

(5) C$_{1-4}$ alkylamino, and C$_{1-4}$ alkyl amino wherein the alkyl moiety is substituted with an hydroxy, and
  (6) guanidino,
  (11) amino, and
(c) aryl C$_{1-3}$ alkyl,
wherein aryl is defined as
  (1) phenyl,
  (2) naphthyl,
  (3) thienyl,
  (4) thiazolyl, and
  (5) benzothienyl,
and wherein the aryl may be mono and di-substituted, the substituents being each independently C$_{1-6}$alkyl, halo, hydroxy, C$_{1-6}$alkyl amino, C$_{1-6}$alkoxy, C$_{1-6}$alkylthio, and C$_{1-6}$alkylcarbonyl;
R$_6$ is selected from the group consisting of:
(a) mono or di substituted Aryl amino,
(b) mono or di substituted Aryl oxy, and
(c) mono or di substituted Aryl thio,
wherein the aryl group is selected from the group consisting of:

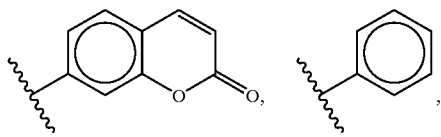

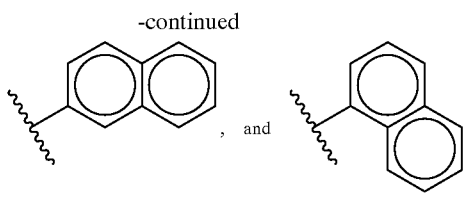, and wherein the substituent is selected from the group consisting of
- (1) H,
- (2) OH,
- (3) $C_{1-3}$alkyl,
- (4) $C_{1-3}$alkyloxy,
- (5) $CO_2H$,
- (6) formyl, and
- (7) CN.

10. A a method of using a compound of claim 9 for determining the interleukin-1β converting enzyme activity of a sample, comprising:

(a) adding, in aqueous solution, in any order,
- (1) a compound of formula I,
- (2) interleukin-1β converting enzyme, and
- (3) a sample; and (b) measuring the interleukin-1β converting enzyme activity of the product of step
- (a) by spectrophotometric or fluorometric means.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Xaa Val Ala Xaa
1

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Xaa Val Ala Asp Xaa
1               5